United States Patent
Salce, Jr. et al.

(10) Patent No.: US 10,463,638 B2
(45) Date of Patent: Nov. 5, 2019

(54) THERAPEUTIC NEUROPATHIC PAIN LOTION

(71) Applicant: SYNERGISTIC THERAPEUTICS, LLC, Naples, FL (US)

(72) Inventors: Anthony H. Salce, Jr., Naples, FL (US); William F. Greenwood, Fairfield, CT (US); Shivsankar Misir, Naples, FL (US)

(73) Assignee: SYNERGISTIC THERAPEUTICS, LLC, Naples, FL (US)

( * ) Notice: Subject to any disclaimer, the term of this patent is extended or adjusted under 35 U.S.C. 154(b) by 0 days.

(21) Appl. No.: 15/951,866

(22) Filed: Apr. 12, 2018

(65) Prior Publication Data

US 2018/0296510 A1 Oct. 18, 2018

Related U.S. Application Data

(60) Provisional application No. 62/484,597, filed on Apr. 12, 2017.

(51) Int. Cl.
| | | |
|---|---|---|
| *A61K 31/485* | (2006.01) | |
| *A61K 31/192* | (2006.01) | |
| *A61K 31/135* | (2006.01) | |
| *A61K 9/06* | (2006.01) | |
| *A61K 47/18* | (2017.01) | |
| *A61K 9/00* | (2006.01) | |
| *A61K 47/22* | (2006.01) | |
| *A61K 45/06* | (2006.01) | |
| *A61K 31/167* | (2006.01) | |
| *A61K 31/195* | (2006.01) | |
| *A61K 31/277* | (2006.01) | |
| *A61K 31/4178* | (2006.01) | |

(52) U.S. Cl.
CPC .......... *A61K 31/192* (2013.01); *A61K 9/0014* (2013.01); *A61K 9/06* (2013.01); *A61K 31/135* (2013.01); *A61K 31/167* (2013.01); *A61K 31/195* (2013.01); *A61K 31/277* (2013.01); *A61K 31/4178* (2013.01); *A61K 45/06* (2013.01); *A61K 47/18* (2013.01); *A61K 47/22* (2013.01)

(58) Field of Classification Search
CPC .................................................. A61K 31/485
See application file for complete search history.

(56) References Cited

U.S. PATENT DOCUMENTS

| | | | |
|---|---|---|---|
| 2002/0035105 A1* | 3/2002 | Caruso | A61K 31/00 514/220 |
| 2003/0133951 A1* | 7/2003 | Coe | A61K 31/4704 424/239.1 |
| 2004/0082543 A1* | 4/2004 | Cheung | A61K 31/12 514/80 |
| 2013/0165468 A1* | 6/2013 | Aung-Din | A61K 9/0014 514/282 |

OTHER PUBLICATIONS

Jorum et al., Pain, 2003, 101(3): 229-235.*

* cited by examiner

*Primary Examiner* — Rei Tsang Shiao
(74) *Attorney, Agent, or Firm* — Moritt Hock & Hamroff LLP; Bret P. Shapiro

(57) ABSTRACT

Technologies are described for a formulation and production of a formulation. The methods may comprise depositing a non-steroidal anti-inflammatory drug (NSAID) compound into a chamber. The methods may comprise depositing a N-methyl-D-aspartate (NMDA) receptor antagonist into the chamber. The methods may comprise respectively depositing a muscle relaxant, a local anesthetic into the chamber, depositing an anticonvulsant into the chamber, depositing an antidepressant into the chamber, and depositing a calcium channel blocking agent into the chamber. The methods may comprise milling the NSAID compound, the NMDA receptor antagonist, the muscle relaxant, the local anesthetic, the anticonvulsant, the antidepressant, and the calcium channel blocking agent into a powder. The methods may comprise adding a solvent with the powder and mixing the solvent with the powder to form a solution. The methods may comprise adding a base cream to the solution and mixing the base cream and the solution to form the formulation.

10 Claims, 2 Drawing Sheets

THERAPEUTIC NEUROPATHIC PAIN LOTION

BACKGROUND

Damage or disease may affect the somatosensory nervous system and may cause neuropathic pain. Abnormal sensations or pain from normally non-painful stimuli may be associated with neuropathic pain and may occur episodically or continuously. Neuropathic pain sensations may include feelings of "stabbings" or "electric shocks", burning, coldness, numbness, itching, and "pins and needles". Common types of neuropathic pain include fibromyalgia, sciatica, diabetic neuropathy, chemo-induced neuropathy, shingles, HIV-induced neuropathy, and neuropathy from injury.

SUMMARY

In some examples formulations are described. The formulations may comprise about 5 to about 10 weight percent of a nonsteroidal anti-inflammatory drug (NSAID). The formulations may comprise about 5 to about 10 weight percent of a N-methyl-D-aspartate (NMDA) receptor antagonist. The formulations may comprise about 2 to about 10 weight percent of a relaxant and antiseptic agent. The formulations may comprise about 2 to about 5 weight percent of a local anesthetic. The formulations may comprise about 3 to about 10 weight percent of an anticonvulsant. The formulations may comprise about 3 to about 5 weight percent of an antidepressant. The formulations may comprise about 0.02 to about 0.05 weight percent of a calcium channel blocking agent.

In some examples, methods to produce a formulation are described. The methods may comprise depositing a nonsteroidal anti-inflammatory drug (NSAID) compound into a chamber. The methods may comprise depositing an N-methyl-D-aspartate (NMDA) receptor antagonist into the chamber. The methods may comprise depositing a relaxant and antiseptic agent into the chamber. The methods may comprise depositing a local anesthetic into the chamber. The methods may comprise depositing an anticonvulsant into the chamber. The methods may comprise depositing an antidepressant into the chamber. The methods may comprise depositing a calcium channel blocking agent into the chamber. The methods may comprise milling the NSAID compound, the NMDA receptor antagonist, the relaxant and antiseptic agent, the local anesthetic, the anticonvulsant, the antidepressant, and the calcium channel blocking agent into a powder. The methods may comprise adding a solvent with the powder in the chamber. The methods may comprise mixing the solvent with the powder in the chamber to form a solution. The methods may comprise adding a base cream to the solution in the chamber. The methods may comprise mixing the base cream and the solution to form the formulation.

In some examples, formulations may be described. The formulations may comprise about 5 to about 10 weight percent of a nonsteroidal anti-inflammatory drug (NSAID). The formulations may comprise about 5 to about 10 weight percent of an N-methyl-D-aspartate (NMDA) receptor antagonist. The formulations may comprise about 2 to about 10 weight percent of a relaxant and antiseptic agent. The formulations may comprise about 2 to about 5 weight percent of a local anesthetic. The formulations may comprise about 3 to about 10 weight percent of an anticonvulsant. The formulations may comprise about 3 to about 5 weight percent of an antidepressant. The formulations may comprise about 0.02 to about 0.05 weight percent of a calcium channel blocking agent. The formulations may comprise a solvent. The formulations may comprise a base cream.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

Figure 1:
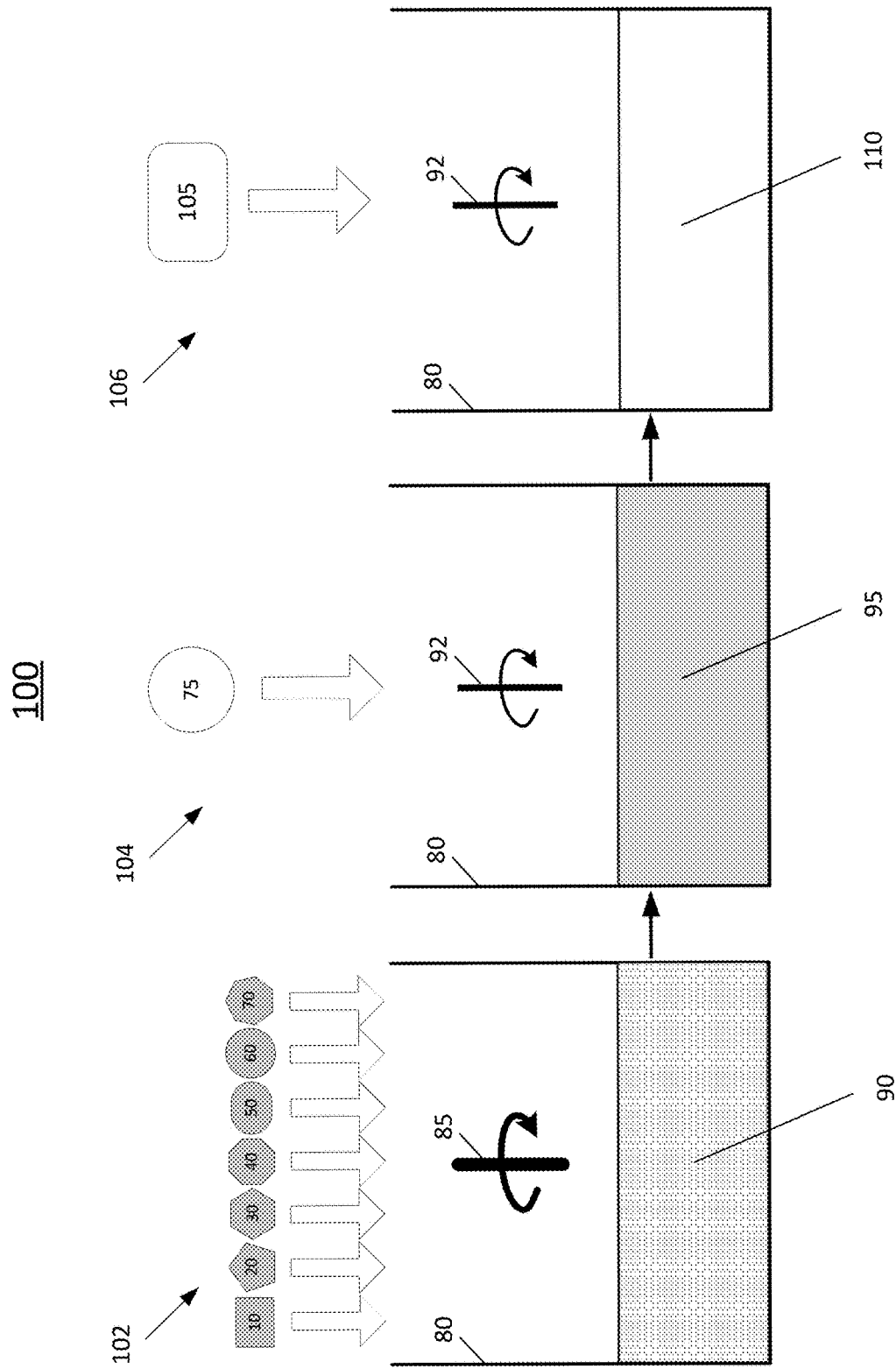
FIG. 1 illustrates an example system that can be utilized to produce a therapeutic neuropathic pain lotion.

all arranged according to at least some embodiments described herein.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

It will be understood that any compound, material or substance which is expressly or implicitly disclosed in the specification and/or recited in a claim as belonging to a group or structurally, compositionally and/or functionally related compounds, materials or substances, includes individual representatives of the group and all combinations thereof.

FIG. 1 illustrates an example system that can be utilized to produce a therapeutic neuropathic pain lotion, arranged in accordance with at least some embodiments presented herein. As discussed in more detail below, a therapeutic neuropathic pain lotion may be effective to provide relief from symptoms of neuropathic pain.

System 100 may include a compound 10, a compound 20, a compound 30, a compound 40, a compound 50, a compound 60, a compound 70, a chamber 80, a milling apparatus 85, and a mixer 92. Compound 10 may be a non-steroidal anti-inflammatory drug (NSAID). Compound 10 may reduce substances in the body that cause pain and inflammation. Compound 10 may inhibit the body's production of prostaglandin to reduce pain and inflammation. Compound 10 may include ketoprofen with formula $C_{16}H_{14}O_3$. Compound 10 may be deposited into chamber 80.

Compound 20 may be an N-methyl-D-aspartate (NMDA) receptor antagonist. Compound 20 may be a general anesthetic, and may also be used for pain management. Compound 20 may decrease peripheral nociceptive signaling through non-competitive blockade of N-methyl-D-aspartate receptors on peripheral nerves. Compound 20 may treat neuropathic pain by providing direct analgesia and may inhibit sympathetically maintained pain. Compound 20 may be ketamine with formula $C_{13}H_{16}ClNO$. Compound 20 may be deposited into chamber 80.

Compound 30 may be a muscle relaxant. Compound 30 may be a structural analog of the inhibitory neurotransmitter gamma-aminobutyric acid (GABA). Compound 30 may exert its effects by stimulation of the gamma-aminobutyric acid receptor subtype B ($GABA_B$). Compound 30 may be dantrolene with formula $C_{14}H_{10}N_4O_5$. Compound 30 may be deposited into chamber 80.

Compound 40 may be a local anesthetic. Compound 40 may be used to locally numb tissue in a specific area. Compound 40 may block a pathway of pain signals along nerves. Compound 40 may stop sodium entering a nerve ending and prevent an electric signal from building up and passing along nerve fibers to the brain. Compound 40 may reduce pain or discomfort caused by skin irritations. Compound 40 may be lidocaine with formula $C_{14}H_{22}N_2O$. Compound 40 may be deposited into chamber 80.

Compound 50 may be an anticonvulsant. Compound 50 may reduce seizures and treat nerve pain. Compound 50 may be an anti-epileptic medication. Compound 50 may affect chemicals and nerves in the body that are involved in the cause of seizures and types of pain. Compound 50 may be used in adults to treat nerve pain caused by herpes virus or shingles. Compound 50 may be gabapentin with formula $C_9H_{17}NO_2$. Compound 50 may be deposited into chamber 80.

Compound 60 may be an antidepressant. Compound 60 may belong to a group of medicines known as tricyclic antidepressants (TCA). Compound 60 may inhibit the mechanism responsible for uptake of serotonin and norepinephrine. Compound 60 may work by increasing the activity of serotonin in the brain. Compound 60 may be amitriptyline with formula $C_{20}H_{23}N$. Compound 60 may be deposited into chamber 80.

Compound 70 may be a calcium channel blocking agent. Compound 70 may be a phenylalkylamine calcium channel blocker and may treat hypertension and cluster headaches. Compound 30 may be an ionic calcium influx inhibitor. Compound 70 may inhibit the transmembrane influx of extracellular calcium ions across the membrane of myocardial cells and vascular smooth muscle cells. Compound 70 may be verapamil with formula $C_{27}H_{38}N_2O_4$. Compound 70, by inhibiting calcium influx, may inhibit the contractile processes, and may thereby dilate the main outer layers of the skin to allow penetration of the topical lotion. Compound 70 may be deposited into chamber 80.

At 102, compound 10, compound 20, compound 30, compound 40, compound 50, compound 60, and compound 70 may be deposited into chamber 80. Compound 10, compound 20, compound 30, compound 40, compound 50, compound 60, and compound 70 may be milled by milling apparatus 85 into a fine powder 90. Compound 10, compound 20, compound 30, compound 40, compound 50, compound 60, and compound 70 may be mixed together by the milling process. Milling and mixing may be performed by milling apparatus 85 either by hand or machine. For example milling apparatus 85 may be a pestle and milling may be performed by hand. In another example milling apparatus 85 may be a milling machine. Powder 90 may include particulates with a particle size from 1 micron to 40 microns.

At 104, a solvent 75 may be added with powder 90 in chamber 80. Solvent 60 may be mixed with powder 80 in chamber 80 by mixer 92 until a clear solution 95 is formed. Solution 95 may include powder 90 dispersed in solvent 75. Mixing may be performed either by hand or machine. For example, mixer 92 may be a hand mixer. In another example, mixer 92 may be a powered mixer such as an electromagnetic mixer. Solvent 75 may include propylene glycol, water, alcohol, or mineral oil and combinations thereof.

At 106, a base cream 105 may be added with solution 95 in chamber 80. Base cream 105 may be mixed with solution 95 in chamber 80 by mixer 92 to form therapeutic neuropathic pain lotion 110. Mixing may be performed either by hand or machine. An amount of base cream 105 may be added in proportion to an amount of solution 95 so as to achieve a desired weigh percentage of compound 10, compound 20, compound 30, compound 40, compound 50, compound 60, and compound 70 respectively in therapeutic neuropathic pain lotion 110. For example, if it is desired for compound 10, compound 20, compound 30, compound 40, compound 50, compound 60, and compound 70 to account for 50 weight percent of therapeutic neuropathic pain lotion 110, then an amount of base cream 105 equal to an amount of solution 95 may be added to solution 95. Base cream 105 may include a moisturizing skin cream. Base cream 105 may include VANICREAM. Base cream 105 may be selected so that base cream 105 includes properties that allow absorption of base cream 105 through the passageways of skin. Base cream 105 may be selected so that base cream 105 may substantially prevent fluid washout of solution 95 from neuropathic pain therapeutic lotion 110. Base cream 105 may be selected so that base cream 105 may provide stability to therapeutic neuropathic pain lotion 110.

Compound 10 may comprise from 5.0% by weight to 10.0% by weight of therapeutic neuropathic pain lotion 110. Compound 20 may comprise from 5.0% by weight to 10.0% by weight of therapeutic neuropathic pain lotion 110. Compound 30 may comprise from 2.0% by weight to 10.0% by weight of therapeutic neuropathic pain lotion 110. Compound 40 may comprise from 2.0% by weight to 5.0% by weight of therapeutic neuropathic pain lotion 110. Compound 50 may comprise from 3.0% by weight to 10.0% by weight of therapeutic neuropathic pain lotion 110. Compound 60 may comprise from 3.0% by weight to 5.0% by weight of therapeutic neuropathic pain lotion 110. Compound 70 may comprise from 0.02% by weight to 0.05% by weight of therapeutic neuropathic pain lotion 110.

Figure 2:
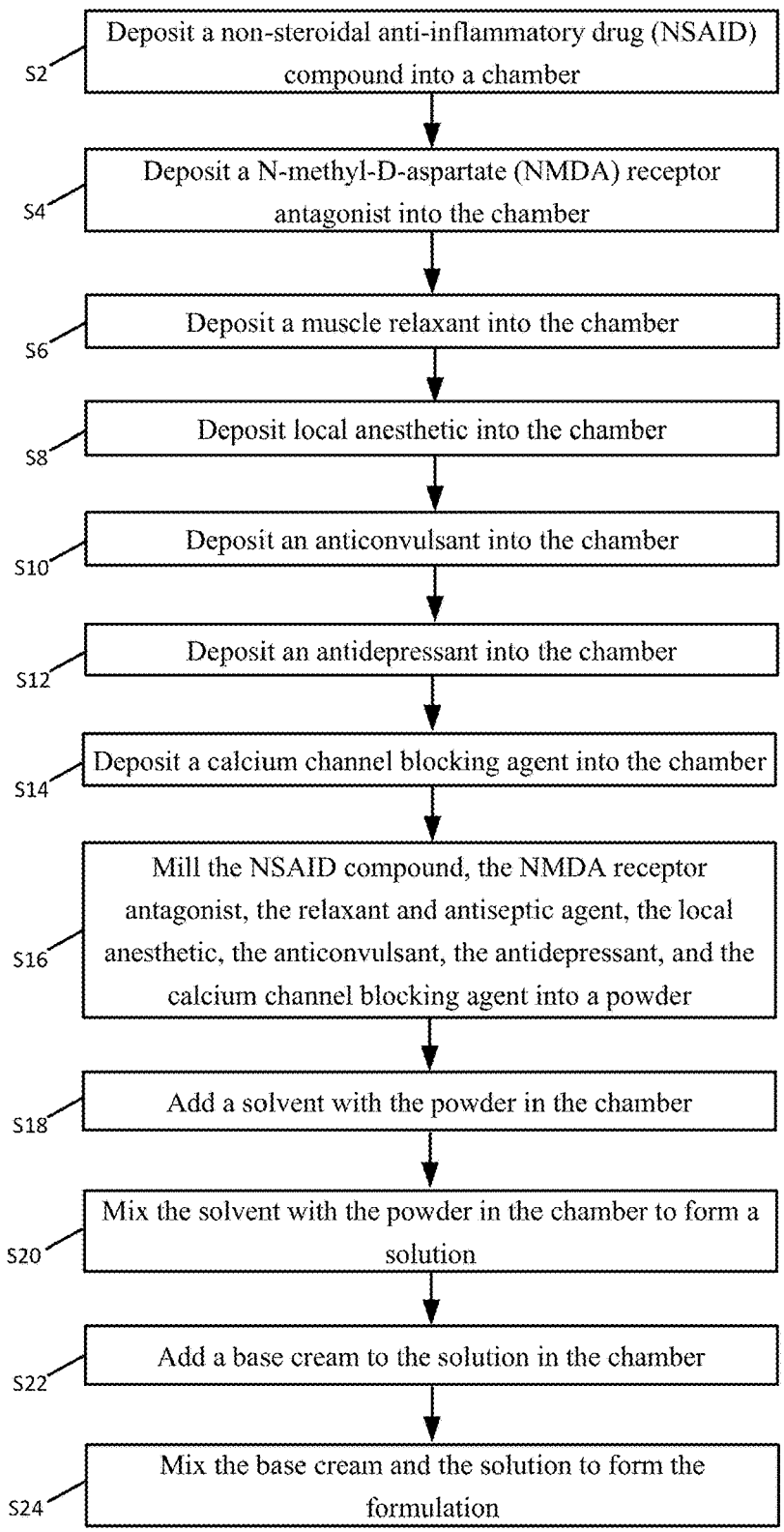
FIG. 2 illustrates a flow diagram of an example process to produce a therapeutic neuropathic pain lotion.

FIG. 2 illustrates a flow diagram of an example process to produce a therapeutic neuropathic pain lotion 110. The process in FIG. 2 could be implemented using, for example, system 100 discussed above. An example process may include one or more operations, actions, or functions as illustrated by one or more of blocks S2, S4, S6, S8, S10, S12, S14, S16, S18, S20 and/or S22. Although illustrated as discrete blocks, various blocks may be divided into additional blocks, combined into fewer blocks, or eliminated, depending on the desired implementation.

Processing may begin at block S2, "Deposit a non-steroidal anti-inflammatory drug (NSAID) compound into a chamber." At block S2, a NSAID compound may be deposited into a chamber. The NSAID compound may reduce substances in the body that cause pain and inflammation. The NSAID compound may inhibit the body's production of prostaglandin to reduce pain and inflammation. The NSAID compound may include ketoprofen with formula $C_{16}H_{14}O_3$.

Processing may continue from block S2 to block S4, "Deposit a N-methyl-D-aspartate (NMDA) receptor antagonist into the chamber." At block S4, an N-methyl-D-aspartate (NMDA) receptor antagonistmay be deposited into the chamber. The N-methyl-D-aspartate (NMDA) receptor antagonist may be a general anesthetic, and may also be used for pain management. The N-methyl-D-aspartate (NMDA) receptor antagonist may decrease peripheral nociceptive signaling through non-competitive blockade of N-methyl-D-aspartate receptors on peripheral nerves. The N-methyl-D-aspartate (NMDA) receptor antagonist may treat neuropathic pain by providing direct analgesia and may inhibit sympathetically maintained pain. The N-methyl-D-aspartate (NMDA) receptor antagonist may be ketamine with formula $C_{13}H_{16}ClNO$.

Processing may continue from block S4 to block S6, "Deposit a muscle relaxant into the chamber." At block S6, a muscle relaxant may be deposited into the chamber. The muscle relaxant may be a structural analog of the inhibitory neurotransmitter gamma-aminobutyric acid (GABA). The muscle relaxant may exert its effects by stimulation of the gamma-aminobutyric acid receptor subtype B ($GABA_B$). The muscle relaxant may be dantrolene with formula $C_{14}H_{10}N_4O_5$.

Processing may continue from block S6 to block S8, "Deposit a local anesthetic into the chamber." At block S8, a local anesthetic may be deposited into the chamber. The local anesthetic may block a pathway of pain signals along nerves. The local anesthetic may stop sodium entering a nerve ending and prevent an electric signal from building up and passing along nerve fibers to the brain. The local anesthetic may reduce pain or discomfort caused by skin irritations. The local anesthetic may be lidocaine with formula $C_{14}H_{22}N_2O$.

Processing may continue from block S8 to block S10, "Deposit an anticonvulsant into the chamber." At block S10, an anticonvulsant may be deposited into the chamber. The anticonvulsant may be an anti-epileptic medication. The anticonvulsant may affect chemicals and nerves in the body that are involved in the cause of seizures and types of pain. The anticonvulsant may be used in adults to treat nerve pain caused by herpes virus or shingles. The anticonvulsant may be gabapentin with formula $C_9H_{17}NO_2$.

Processing may continue from block S10 to block S12, "Deposit an antidepressant into the chamber." At block S12, an antidepressant may be deposited into the chamber. The antidepressant may belong to a group of medicines known as tricyclic antidepressants (TCA). The antidepressant may inhibit the mechanism responsible for uptake of serotonin and norepinephrine. The antidepressant may work by increasing the activity of serotonin in the brain. The antidepressant may be amitriptyline with formula $C_{20}H_{23}N$.

Processing may continue from block S12 to block S14, "Deposit a calcium channel blocking agent into the chamber." At block S6, a calcium channel blocking agent may be deposited into the chamber. The calcium channel blocking agent may be a phenylalkylamine calcium channel blocker and may treat hypertension and cluster headaches. The calcium channel blocking agent may be an ionic calcium influx inhibitor. The calcium channel blocking agent may inhibit the transmembrane influx of extracellular calcium ions across the membrane of myocardial cells and vascular smooth muscle cells. The calcium channel blocking agent may inhibit the contractile processes, and may thereby dilate the main outer layers of the skin to allow penetration of a topical lotion. The calcium channel blocker may be verapamil with formula $C_{27}H_{38}N_2O_4$.

Processing may continue from block S14 to block S16, "Mill the NSAID compound, the NMDA receptor antagonist, the relaxant and antiseptic agent, the local anesthetic, the anticonvulsant, the antidepressant, and the calcium channel blocking agent into a powder." At block S16, the NSAID compound, the NMDA receptor antagonist, the relaxant and antiseptic agent, the local anesthetic, the anticonvulsant, the antidepressant, and the calcium channel blocking agent may be milled into a fine powder. The NSAID compound, the NMDA receptor antagonist, the relaxant and antiseptic agent, the local anesthetic, the anticonvulsant, the antidepressant, and the calcium channel blocking agent may be mixed while being milled into a fine powder. The milling and mixing may be performed either by hand or machine. The powder may include particulates with a particle size from 1 micron to 40 microns.

Processing may continue from block S16 to block S18, "Add a solvent with the powder in the chamber." At block S18, a solvent may be added to the powder in the chamber. The solvent may include propylene glycol, water, alcohol, or mineral oil and combinations thereof.

Processing may continue from block S18 to block S20, "Mix the solvent with the powder in the chamber to form a solution." At block S20, the solvent may be mixed with the powder in the chamber. The solvent may be mixed with the powder in the chamber until a clear solution is formed with the powder dispersed in the solvent to form a solution. Mixing may be performed either by hand or machine.

Processing may continue from block S20 to block S22, "Add a base cream to the solution in the chamber." At block S18, a base cream may be added to the solution in the chamber. An amount of the base cream may be added in proportion to an amount of the solution in the chamber so as to achieve a desired weigh percentage of the NSAID compound, the NMDA receptor antagonist, the relaxant and antiseptic agent, the local anesthetic, the anticonvulsant, the antidepressant, and the calcium channel blocking agent respectively in the formulation. The base cream may include a moisturizing skin cream. The base cream may include VANICREAM. The base cream may substantially allow absorption of the base cream through the passageways of skin. The base cream may substantially prevent fluid washout of the solution in the formulation. The base cream may provide stability to the formulation.

Processing may continue from block S22 to block S24, "Mix the base cream and the solution to form the formulation." At block S24, the base cream may be mixed with the solution to form the formulation.

A system in accordance with the present disclosure may be an effective to produce a topical treatment for neuropathic pain. An embodiment of the present application may be highly stable and provide high skin penetration. An embodiment of the present application may provide a rapid achievement of NSAID and NMDA receptor antagonist concentration in a user's blood. A system in accordance with the present disclosure may provide a treatment without irritation. An embodiment of the present application may be effective for the treatment of neuropathic pain with complete dissolution of the active NSAID and NMDA receptor antagonist. In some cases, a therapeutic neuropathic pain lotion may be preferred over another treatment form, such as an oral pill.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A formulation for a topical lotion_ comprising:
 a nonsteroidal anti-inflammatory drug (NSAID), wherein the NSAID is ketoprofen;
 a N-methyl-D-aspartate (NMDA) receptor antagonist, wherein the NMDA receptor antagonist is ketamine;
 a muscle relaxant, wherein the muscle relaxant is dantrolene;
 a local anesthetic, wherein the local anesthetic is lidocaine;
 an anticonvulsant, wherein the anticonvulsant is gabapentin;
 an antidepressant, wherein the antidepressant is amitriptyline; and
 a calcium channel blocking agent, wherein the calcium channel blocking agent is verapamil; and
 wherein the formulation produces a topical lotion treatment for neuropathic pain.

2. The formulation of claim 1, comprising about 5 to about 10 weight percent of the ketoprofen.

3. The formulation of claim 1, comprising about 5 to about 10 weight percent of the ketamine.

4. The formulation of claim 1, comprising about 2 to about 10 weight percent of the dantrolene.

5. The formulation of claim 1, comprising about 2 to about 5 weight percent of the lidocaine.

6. The formulation of claim 1, comprising about 3 to about 10 weight percent of the gabapentin.

7. The formulation of claim 1, comprising about 3 to about 5 weight percent of the amitriptyline.

8. The formulation of claim 1, comprising about 0.02 to about 0.05 weight percent of the verapamil.

9. The formulation of claim 1, further comprising a solvent, wherein the solvent includes propylene glycol, water, alcohol, mineral oil, or combinations thereof.

10. The formulation of claim 1, comprising:
 about 5 to about 10 weight percent of the ketoprofen;
 about 5 to about 10 weight percent of the ketamine;
 about 2 to about 10 weight percent of the dantrolene;
 about 2 to about 5 weight percent of the lidocaine;
 about 3 to about 10 weight percent of the gabapentin;
 about 3 to about 5 weight percent of the amitriptyline;
 about 0.02 to about 0.05 weight percent of the verapamil;
 a solvent; and
 a base cream.

* * * * *